United States Patent [19]

Drouet et al.

[11] Patent Number: 5,021,349
[45] Date of Patent: Jun. 4, 1991

[54] CULTURE MEDIUM CONTAINING HUMAN ALBUMIN, PROCESS FOR THE PREPARATION OF AN INJECTABLE PRODUCT FROM THIS MEDIUM, PRODUCT OBTAINED AND ITS USE, AND COMPOSITION OBTAINED

[75] Inventors: Xavier Drouet; Dominique Goossens, both of Paris; Philippe Rouger, Chaville, all of France

[73] Assignee: Foundation Centre National De Transfusion Sanguine, Paris, France

[21] Appl. No.: 61,706

[22] Filed: Jun. 11, 1987

[30] Foreign Application Priority Data

Jun. 12, 1986 [FR] France ............................... 86 08494

[51] Int. Cl.$^5$ .............................................. C12N 5/00
[52] U.S. Cl. ............................ 435/240.31; 435/240.2; 435/240.3
[58] Field of Search .............. 435/68, 1, 172.2, 240.27, 435/240.31, 240.2, 240.3; 530/387; 436/547, 548; 424/85; 935/107

[56] References Cited

U.S. PATENT DOCUMENTS 4,198,479  4/1980  Tytell et al. .............................. 435/2
4,681,848  7/1987  Tsukamoto et al. .................. 435/68

FOREIGN PATENT DOCUMENTS 0060565  9/1982  European Pat. Off. .
8502413  10/1985  PCT Int'l Appl. .
2127434  4/1984  United Kingdom ................ 530/387

OTHER PUBLICATIONS

Kawamoto et al., 1983, *Analytical Biochemistry 130*, pp. 445–453 "Development of a Serum Free Medium for Growth of NS1 Mouse Myeloma Cells and Its Application to the Isolation of NS1 Hybridomas".

Iscove et al., "Complete Replacement of Serum by Albumin, Transferrin, and Soybean Lipid in Cultures of Lipopolysaccharide-Reactive B Lymphocytes", J. Exp. Med. vol. 147, 923–933, 1978.

*Chemical Abstracts*, vol. 101, No. 25, Dec. 17, 1984, p. 399, "Culture of Human Lymphocytes in Serum-Free Medium".

*Pharmacia Fine Chemicals*, Presentations from Biotech '83, May 4–6, 1983, pp. 39–46, "Purification of Monoclonal Antibodies and Their Use in the Isolation of Biological Products".

*Proceedings of the National Academy of Science*, U.S.A., vol. 53, 1965 pp. 288–293, "Clonal Growth of Mammalian Cells in a Chemically Defined, Synthetic Medium."

Primary Examiner—Elizabeth C. Weimar
Assistant Examiner—Gail Poulos
Attorney, Agent, or Firm—Blakely, Sokoloff, Taylor & Zafman

[57] ABSTRACT

The present invention relates to a lymphoblastoid cell culture medium making it possible in particular to prepare products which can be administered to man by intravenous injection, the said culture medium containing, in addition to the constituent components of IS-COVE's medium, only human albumin as protein.

6 Claims, No Drawings

CULTURE MEDIUM CONTAINING HUMAN ALBUMIN, PROCESS FOR THE PREPARATION OF AN INJECTABLE PRODUCT FROM THIS MEDIUM, PRODUCT OBTAINED AND ITS USE, AND COMPOSITION OBTAINED

The present invention relates to a lymphoblastoid cell culture medium making it possible in particular to obtain a product which can be administered to man by intravenous injection.

The present invention was achieved more particularly in the context of researches concerning the maternal-fetal blood group incompatibilities associated with the Rhesus factor.

Blood groups are antigenic systems located on the surface of the erythrocytes; they include the Rhesus group based essentially on the Rh(D) antigen, which has been known since 1939 as the Rhesus factor. People who possess this antigen are said to be Rhesus positive (Rh+) and represent 85% of the caucasian population, the others being Rhesus negative (Rh−).

There are two essential reasons why the Rh(D) factor is important:

1—The D antigen possesses strong antigenic properties.

2—The gene coding for the D antigen is transferred according to the laws of genetics and behaves as a dominant factor.

In particular, a child produced by an Rh− woman (15% of women) and an Rh+ man (85% of men) is Rh+ in 75% of cases.

Therefore, an Rh− mother can bear an Rh+ child in a very large number of cases. For a variety of reasons, and especially at childbirth, this Rh+ antigen can enter the mother's bloodstream, causing her to develop an alloimmunity.

In the event of a further pregnancy, the antibodies thus produced may enter the bloodstream of the fetus and react with its cells to cause massive hemolysis.

At present, in the case of a pregnancy where there is a risk of maternal-fetal incompatibility, anti-Rh(D) antibodies are injected. This injection makes it possible to neutralize any antigen-carrying red blood cells passing from the fetus to the mother and hence to limit the risks that the mother will develop immunity.

Hitherto, these anti-Rhesus antibodies have been obtained from blood donated by Rh− subjects who have had an Rh+ fetus or subjects who have been brought into contact in some other way with the antigens in question. It can be understood that these sources of antibodies are unsatisfactory for a very large number of reasons; this is why we have resorted to the technique of monoclonal antibodies, which enables this type of antibody to be prepared from cell cultures.

The techniques for the preparation of clones capable of secreting human monoclonal antibodies are now fairly well known and do not need to be described in detail.

One of the important problems encountered in the preparation of these monoclonal antibodies is the fact that cell cultures involve the use of proteins in the culture media, which are difficult to remove at a later stage. Although this is only a minor disadvantage in diagnostic kits, it can become a major disadvantage when it comes to antibodies used in therapy, especially if they are to be injected.

In the case of injection, especially intravenous injection, the presence of heterologous proteins can in fact cause serious disorders, limiting the possibilities of using the corresponding products.

Now, maternal-fetal incompatibilities are just such a case where it is very desirable to use intravenous injections.

One of the objects of the present invention is in fact to permit the preparation of monoclonal antibodies capable of being injected into humans.

More particularly, the present invention relates to a novel culture medium which makes it possible to produce a product, such as human monoclonal antibodies, from supernatants of cultures of lymphoblastoid cell clones.

The description which follows will refer essentially, as an example, to the preparation of monoclonal antibodies for therapeutic purposes, but this medium can of course be used to prepare monoclonal antibodies for other purposes, for example diagnosis.

The novel composition of the medium according to the present invention enables the said product to be prepared in such a way that it can be injected into man, i.e. so that it is devoid of animal proteins and toxic products. To achieve this, the culture medium according to the present invention contains, in addition to the constituent components of a lymphoblastoid cell culture medium, in particular Iscove's medium, only human albumin as protein.

Iscove's medium, which is used to carry out the present invention, is known to those skilled in the art. It is "Iscove Modified Dulbecco's Medium" (reference: N. N. Iscove and F. Melchers, Complete replacement of serum by albumin transferrin and soybean lipid in cultures of lipopolysaccharide-reactive B lymphocytes, J. Exp. Med 147, 928-933, 1978), the composition of which will be given in detail in Example 1.

To this medium, it is preferred, according to the present invention, to add plasmatic human albumin (produced for example by the National Blood Transfusion Center), which corresponds to Cohn's fraction V and has the following characteristics:

powder
moisture content $\bar{m}2$: 3%
electrophoretic purity: >97.5%
level of residual G immunoglobulins: <1%°
level of alcohol: <1.5 g/l for a 10% solution
devoid of a marker for the Hbs antigen and the LAV/HTLV III virus.

This albumin can be in solution from the outset. It is used at a concentration of the order of 10 to 9000 mg/l, for example 100–700 mg/l and preferably 350 mg/l.

The medium according to the present invention can also contain the following components:

at least one unsaturated fatty acid. Linoleic acid can be used here at a concentration of the order of 0.09 to 14 mg/l and preferably 2.8 mg/l. The linoleic acid can be replaced with the same doses of oleic acid, palmitoleic acid and arachidonic acid.

at least one mercaptan at a dose of between 0.1 and 150 μM. 2-Mercaptoethanol or glutathion can be used. According to the present invention, it is preferred to use monothioglycerol at a dose of 75 μM.

at least one monoamine selected from ethanolamine, at a dose of between 300 nM and 100 μM, preferably 20 μM, and phosphoethanolamine, at a concentration of between 5 and 1000 μM.

at least one diamine. This can be 1,4-diaminobutane or diaminopentane at a dose of between 100 nM and 100 μM, preferably 10 μM. It is also possible to use spermine or spermidine at a concentration of between 10 nM and 100 μM.

The preferred medium according to the present invention, hereafter called SA medium, is Iscove's medium to which 350 mg/l of plasmatic human albumin (Cohn's fraction V—NBTC method), 2.8 mg/l of linoleic acid, 75 μM of monothioglycerol, 20 μM of ethanolamine and 10 μM of 1,4-diaminobutane have been added.

This medium can also be complemented by the addition of one or more ribonucleosides, for example at a concentration of 1 to 100 mg/l.

This medium enables human monoclonal antibodies to be produced from supernatants of lymphoblastoid cell cultures, this composition making it possible to prepare a product, devoid of side effects, which can be injected into man.

Comparative studies on the culture of the cell clone H2D5D2 were made between the SA medium according to the present invention and the conventional medium.

The conventional medium is Iscove's medium to which 20% of fetal calf serum is added.

The clone H2D5D2 secretes a monoclonal antibody directed against the Rhesus (D) factor.

Until now, it was impossible to cultivate this clone without adding fetal calf serum to Iscove's medium in a proportion of 20%.

The comparative studies show that the SA medium according to the present invention leads to a culture of the cell clone H2D5D2 which is virtually identical to that afforded by the conventional medium, from both the qualitative and quantitative point of view.

As one of the objects of this SA culture medium according to the present invention is to make it possible to purify a product such as a monoclonal antibody, and in particular H2D5D2, to give a product which can be administered to man by intravenous injection, the present invention also relates to the process for the preparation and formulation of the said product.

Thus, after the desired product, such as the monoclonal antibody, has been obtained in the supernatant of a culture effected in SA medium, the following steps for purifying and formulating the said product are carried out:

A filtration-concentration step in which it is possible to carry out one or more filtrations and then a concentration of the product, enabling the latter to be varied by a factor of about 10 to a factor of about 50. As far as the filtrations are concerned, they can be carried out successively on two membranes of 0.2 U and 0.1 U.

A purification step in which the product is subjected at least once to chromatography on protein A Sepharose and then, if appropriate, on an ion exchange column.

A formulation step in which the material is filtered on a 0.2 U membrane and then diluted in order to adjust the concentrations. Following this dilution, albumin is added at a concentration which can vary from about 4 to 10 g/liter. Finally, the product can be spread for lyophilization.

The present invention also relates to the product obtained by the above-mentioned process. This is preferably the anti-D monoclonal antibody in particular, such as H2D5D2. it can be a mixture of several clones having the same antibody specificity. It is also possible to use this type of medium for the culture of other cells, for example that mentioned in Patent WO85/02413.

Finally, the present invention relates to the use of this product for the preparation of pharmaceutical compositions, especially those which can be administered by intravenous injection, and to the compositions obtained. Apart from the product representing the active principle, these pharmaceutical compositions contain pharmaceutically acceptable excipients for converting them to pharmaceutical formulations. In particular, it is possible to use a solution of active principle based on physiological sodium chloride.

The present invention will be understood more clearly from the description of the example which follows.

EXAMPLE

The experiments below are comparative experiments between the SA medium according to the invention and the conventional medium, i.e.: Iscove's medium+fetal calf serum (20%).

| ISCOVE'S MODIFICATIONS TO DULBECCO'S MEDIUM | |
| --- | --- |
| AMINO ACIDS | mg/l |
| L-Aspartic acid | 30.00 |
| L-Glutamic acid | 75.00 |
| L-Alanine | 25.00 |
| L-Arginine.HCl | 84.00 |
| L-Asparagine.H$_2$O | 28.40 |
| Disodium L-cystine | 82.80 |
| L-Glutamine | 584.00 |
| Glycocoll | 30.00 |
| L-Histidine.HCl.H$_2$O | 42.00 |
| L-Isoleucine | 105.00 |
| L-Leucine | 105.00 |
| L-Lysine.HCl | 146.00 |
| L-Methionine | 30.00 |
| L-Phenylalanine | 66.00 |
| L-Proline | 40.00 |
| L-Serine | 42.00 |
| L-Threonine | 95.00 |
| L-Tryptophan | 16.00 |
| L-Tyrosine | 83.80 |
| L-Valine | 94.00 |
| VITAMINS | mg/l |
| Folic acid | 4.00 |
| Biotin | 0.013 |
| Choline chloride | 4.00 |
| I-Inositol | 7.20 |
| Nicotinamide | 4.00 |
| Calcium D-pantothenate | 4.00 |
| Pyridoxal.HCl | 4.00 |
| Riboflavin | 0.40 |
| Thiamine.HCl | 4.00 |
| Vitamin B12 | 0.013 |
| SALTS AND OTHER COMPONENTS | mg/l |
| CaCl$_2$ | 165 |
| KCl | 330.00 |
| KNO$_3$ | 0.076 |
| MgSO$_4$7H$_2$O | 200.00 |
| NaCl | 4505 |
| NaHCO$_3$ | 3024 |
| NaH$_2$PO$_4$.2H$_2$O | 162.5 |
| D-Glucose | 4500.00 |
| HEPES | 5958.00 |
| Sodium pyruvate | 110.00 |
| Sodium selenite | 0.0173 |
| Phenol red | 15.00 |

The cell clone H2D5D2 was subjected to 10 passes, starting from a concentration of $0.5 \times 10^6$ cells/ml for each subculture. Irrespective of the medium, the inoculum is strictly identical and prepared in the absence of fetal calf serum.

These results are reported in Tables no. 1, 2 and 3.

Table 1: Determination of the cell concentration and the viability during 10 successive passes.

Table 2: Determination of the level (Ug/ml) of anti-D immunoglobulins in the supernatants (D7) of a culture obtained in a 500 ml roller (R500). The method used is that of the CNRGS, in accordance with the recommendations of the pharmacopeia.

Table 3: Culture of $H_2D_5D_2$ lymphoblastoid cells in flask of 75 cm$^3$: Comparison between SA medium and standard medium containing 20% of fetal calf serum. This comparison shows the quadrupling of the productivity when the SA medium is used.

supernatants yields products which can be injected into man without side effects.

TABLE 3

| Subculture N° | Concentration of cells at J3-J4 (10$^6$/ml) | | Concentration of IgG at J7 (μm/ml) | |
|---|---|---|---|---|
| | medium SA | medium SVF 20% | medium SA | medium SVF 20% |
| 1 | 2.05 | 3.01 | — | — |
| 2 | 1.25 | 2.18 | — | — |
| 3 | 1.15 | 2.79 | 44 | 4.4 |
| 4 | 1.49 | 1.92 | 71.2 | 14.3 |
| 5 | 1.26 | 2.82 | 49.4 | 18.1 |
| 6 | 1.06 | 2.13 | 43.4 | 14.4 |
| 7 | 1.0 | 2.40 | 39 | 8.1 |
| Mean + E.T. | 1.32 + 0.36 n = 7 | 2.46 + 0.41 n = 7 | 49.4 + 12.8 n = 5 | 11.9 + 5.5 n = 5 |

Legends:
J3, J4 and J7: Days 3, 4 and 7 after the beginning of the culture
SVF: fetal calf serum

TABLE 1

| | | Iscove's medium + 20% of fetal calf serum | | SA medium | | |
|---|---|---|---|---|---|---|
| | | Cell concentration | Viability | Cell concentration | Viability | Technique |
| I | D$_3$ | 2.27 · 10$^6$ | 94% | 1.37 · 10$^6$ | 83% | Flask 100 |
| II | D$_3$ | 2.35 · 10$^6$ | 94% | 1.24 · 10$^6$ | 76% | Flask 150 |
| III | D$_4$ RI | 3 · 10$^6$ | 93% | 1.53 · 10$^6$ | 70% | Roller 500 |
| | D$_4$ FIII | 1.7 · 10$^6$ | 88% | 1.13 · 10$^6$ | 76% | Flask 120 |
| IV | D$_4$ RII | 2.5 · 10$^6$ | 95% | 1.62 · 10$^6$ | 82% | Roller 500 |
| | D$_4$ FIV | 1.36 · 10$^6$ | 94% | 1.14 · 10$^6$ | 86% | Flask 150 |
| V | D$_4$ RIII | 3.85 · 10$^6$ | 93% | 2 · 10$^6$ | 79% | Roller 500 |
| | FV | 2.15 · 10$^6$ | 90% | 1.56 · 10$^6$ | 75% | Flask 100 |
| VI | D$_3$ RIV | 2.53 · 10$^6$ | 95% | 2.07 · 10$^6$ | 84% | Roller 500 |
| | FVI | 1.93 · 10$^6$ | 95% | 1.51 · 10$^6$ | 80% | Flask 100 |
| VII | D$_4$ RV | 3.45 · 10$^6$ | 94% | 2.52 · 10$^6$ | 86% | Roller 500 |
| | FVII | 2.66 · 10$^6$ | 90% | 1.92 · 10$^6$ | 80% | Flask 100 |
| VIII | D$_3$ RVI | 2.2 · 10$^6$ | 94% | 1.5 · 10$^6$ | 83% | Roller 500 |
| | FVIII | 2.02 · 10$^6$ | 92% | 1.21 · 10$^6$ | 80% | Flask 100 |
| IX | D$_4$ RVII | 4.06 · 10$^6$ | 93% | 2.47 · 10$^6$ | 79% | Roller 500 |
| | FIX | 2.7 · 10$^6$ | 90% | 1.40 · 10$^6$ | 71% | Flask 100 |
| X | D$_4$ RVIII | 4.15 · 10$^6$ | 95% | 2.42 · 10$^6$ | 80% | Roller 500 |
| | FX | 2.7 · 10$^6$ | 89% | 1.59 · 10$^6$ | 73% | Flask 100 |

Legends:
R: roller (also called rolling bottle)
F: flask
Roman numeral: represents the pass rank
D: number of days since the culture was started

TABLE 2

| Pass | Iscove's medium + 20% of fetal calf serum | SA medium |
|---|---|---|
| II | 11.2 | 11.2 |
| III | 16.8 | 11.2 |
| IV | 25.2 | 33.6 |
| V | 31.5 | 19.5 |
| VI | 21 | 15.7 |
| VI | 25.2 | 19.6 |
| VIII A | 20 | 30 |
| VIII B | 20 | 13.5 |
| Mean ± standard deviation | 21.4 ± 6.1 | 19.3 ± 8.4 |
| Student test | p > 0.5 | |

These tests demonstrate that SA medium permits cultures under conditions which are virtually identical to those used for the traditional media, but without requiring the use of animal proteins. Purification of the

What is claimed is:

1. A lymphoblastoid cell culture medium making it possible in particular to prepare products which can be administered to man by intravenous injection, this said culture medium containing, in addition to the constituent components of Iscove's medium, only human albumin protein in a proportion of 100 to 700 mg/l, and at least one unsaturated fatty acid selected from the group consisting of linoleic acid, oleic acid, arachadonic acid and palmetoleic acid, at a concentration from 0.09 to 14 mg/l, and one diamine selected from the group consisting of spermidine and spermine at a concentration from 10 nM to 100 μM and 1.4 diaminobutane and diaminopentane in a concentration from 100 nM to 100 μM.

2. The medium as in claim 1, which also contains at least one mercaptan selected from the group consisting of monothioglycerol, mercaptoethanol and gluetthion in a concentration between 0.1 and 150 μM and one monamine selected from the group consisting of ethanolamine at a concentration of between 300 nM and 100 μM and phosphoethanolamine at a concentration of between 5 μM and 100 μM.

3. The medium as in claim 2, wherein the mercaptan is monothioglycerol at a dose of 75 μM.

4. The medium as in claim 1, wherein the diamine is provided at a concentration of 10 μM.

5. The medium as in claim 1, wherein said human albumin protein is 350 mg/l of plasmatic human albumin, said unsaturated fatty acid is 2.8 mg/l of linoleic acid, and wherein said medium further comprises 75 μM of monothioglycerol, 20 μM ethanolamine and 10 μM of 1,4-diaminobutane.

6. The medium as claimed in claim 1, which also contains one or more ribonucleosides at a concentration of between 1 and 100 mg/l.

* * * * *